United States Patent [19]

Cibis

[11] Patent Number: 4,498,003
[45] Date of Patent: Feb. 5, 1985

[54] DEVICE FOR TESTING THE RIMS OF BOTTLE APERTURES FOR FLAWS

[75] Inventor: Johannes Cibis, Mintraching, Fed. Rep. of Germany

[73] Assignee: Krones A.G. Hermann Kronseder Maschinenfabrik, Neutraubling, Fed. Rep. of Germany

[21] Appl. No.: 443,094

[22] Filed: Nov. 19, 1982

[30] Foreign Application Priority Data

Nov. 27, 1981 [DE] Fed. Rep. of Germany ....... 3147086

[51] Int. Cl.³ .............................................. G01N 21/90
[52] U.S. Cl. ................................. 250/223 B; 356/240
[58] Field of Search .............................. 250/223 B, 227; 356/240, 426; 209/526

[56] References Cited

U.S. PATENT DOCUMENTS

| | | | |
|---|---|---|---|
| 3,533,704 | 10/1970 | Krenmayr | 356/240 |
| 4,213,702 | 7/1980 | Bryant et al. | 250/223 B |
| 4,284,353 | 8/1981 | Yoshida et al. | 250/223 B |
| 4,293,219 | 10/1981 | Ducloux | 250/223 B |

Primary Examiner—David C. Nelms
Assistant Examiner—J. J. Brophy
Attorney, Agent, or Firm—Fuller, House & Hohenfeldt, S.C.

[57] ABSTRACT

In a device for testing the rim around the apertures of bottles for flaws there is a rotor which has an optic fiber bundle for transmitting light to the rim or sealing surface of the bottle and another fiberoptic bundle for receiving light reflected or scattered by the surface that is to be sealed with a crown cap. The optical axes of the light transmitter and receiver are arranged in a common scanning plane which is substantially perpendicular to the plane of the aperture or rim and intersects the plane tangentially to the sealing surface. The optical axes are inclined by an acute angle, alpha, with respect to the plane of the aperture or rim. The light transmitter and receiver optical bundles have lenses at their ends for, respectively, projecting a light beam through the aperture plane and for receiving light reflected or scattered therefrom. One end of the light conductor or transmitter is coupled to a light source. One end of the light receiver is coupled to a photosensitive device. The bottles are rotated at high speed during a scanning and testing cycle. If a flaw is present, the light reflected from the rim of the aperture drops below a threshold level. This event results in producing electric signals that operate an ejection device for removing the bottle from the series of bottles that are being inspected.

9 Claims, 4 Drawing Figures

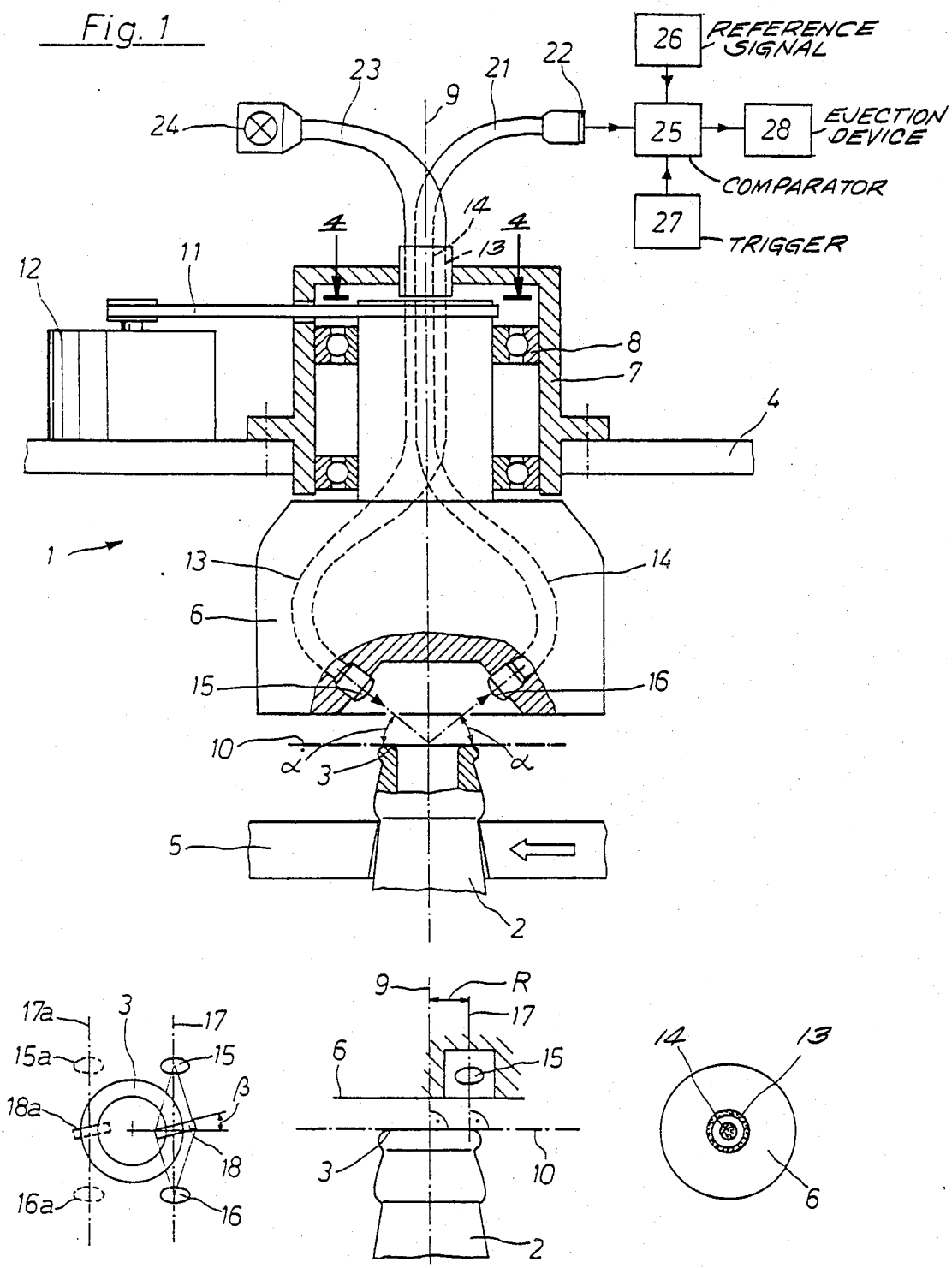

DEVICE FOR TESTING THE RIMS OF BOTTLE APERTURES FOR FLAWS

BACKGROUND OF THE INVENTION

This invention relates to a device for testing the condition of the glass rim surrounding the apertures of bottles where the bottles are capped or otherwise sealed. Reliable detection of flaws in the sealing surface of bottle apertures is one of the greatest problems in the field of bottle inspection. On one hand, even the smallest cracks and chips or other defects which could impair tight seating and sealing of the bottle closure must be reliably detected. On the other hand, testing must not be adversely affected by differences in material, or by the shape of the bottles, or by bubbles below the sealing surface, or by different relative positions between the bottle aperture and the test device. Moreover, there should be no erroneous rejection of the bottles that have a good sealing surface around the aperture. Finally, the testing device should be simple in construction, reliable in operation, and be able to test the condition of the body of the bottle and, particularly, the rim around the sealing aperture at rates of 40,000 bottles per hour or more in a single inspection machine. Simultaneous fulfillment of all of these requirements was not possible before the present invention was made.

There is a known bottle aperture rim condition tester in which there is a mirror aligned with a rotor shaft, said mirror projecting a beam of light from a source of light also lying in the rotor shaft, slantingly out from above in a radial direction onto the rim or sealing surface of the bottle aperture (German Laid Open specification No. 24 11 723). From there, the beam is reflected essentially outwardly to a semiconductor or photoelectric detector such as a solar cell. The inspection field on the aperture rim that is illuminated by the light transmitting mirror is developed approximately rectangularly and rotates with the rotor. As it is sometimes wider than the aperture or sealing surface, respectively, it may be moved somewhat forward during testing, as this is necessary for the attainment of high yields. In this known device, the beam of light on the aperture of the single test channel engaging the entire aperture is scattered from any smooth and regular zone on account of the curvatures of the sealing surface so that the effective surface of the light detector must be very large. This leads to the fact that even the light reflected from a damaged point or zone around the aperture encounters the light detector to some extent, and therefore, reduction of light intensity upon scanning of a damaged zone is often very slight and sometimes is not actually detectable. The ability of this known device to detect points of damage of all types is therefore insufficient.

There is another known device for testing bottle apertures comprising a rotor rotating concentrially to the bottle axis. Several cooperating pairs of light transmitters and light receivers or detectors are arranged on the rotor and these travel over a determined annularly shaped partial area of the bottle aperture or sealing surface, respectively. This device is described in U.S. Pat. No. 3,349,906. The sensitivity of the patented apparatus, because of utilizing a plurality of test channels, should be quite high. However, a disadvantage is that there is a strong influence on the test results by deviations of the aperture position from an ideal position and from the contour of the bottle aperture rims differing from an ideal form. These deviations lead to frequent rejection of flawless bottles. The complicated construction and cumbersome selection of a rotor with its plurality of light-receivers and the corresponding problematical connection of the receiver with the stationary readout device is another unfavorable characteristic.

SUMMARY OF THE INVENTION

The main object of the invention is to provide a device for testing bottle aperture rims or sealing surfaces for flaws which device is simple in construction because of it employing only a single test channel for the entire sealing surface to thereby increase substantially the capability of recognizing or detecting flaws and other irregularities around the aperture.

In accordance with the invention, the optical axes of a light transmitter and a light receiver are in a tangential plane and comprise the single testing channel so that all types of large and small flaws in the rim around the aperture may be recognized with high reliability, especially in the particularly important upper and middle area of the sealing surface. The smallest chips or splinterings-off lead to a large reduction in the radiation directed to the light receiver, while with flawless apertures, in spite of differences in the rim shape, or in the material, or in the position of the aperture relative to the testing device, no significant changes in the received radiation occur. Therefore, high yields may be obtained and the number of erroneous discards is low. This good result is not impaired by slight deviations of the tangential scanning plane from a vertical attitude. The size of these deviations is dependent on the shape of the bottle aperture and may still be called "substantially vertical." Having the optical axis of the transmitted light beam and also of the light beam reflected to the detector at an angle of ten to forty degrees relative to the plane of the rim around the aperture is particularly advantageous. This is an optimal compromise between the requirements for high reliability on one hand and low dependence on the form and position of the bottle aperture on the other hand.

A further advantage is that the characteristic seam points in the sealing surface are almost completely compensated so that they do not influence the test results.

How the foregoing and other objects of the invention are achieved will be evident in the description of a preferred embodiment of the invention which will now be set forth in reference to the drawing.

DESCRIPTION OF THE DRAWING

FIG. 1 is a side elevational view, partly in section, of a device for testing the rims around bottle apertures for flaws;

FIG. 2 is a diagrammatic plan view of a bottle aperture showing the optic geometry and the position of the inspection zone;

FIG. 3 is a side view of a bottle aperture on which the position of the scanning plane is identified; and FIG. 4 is a transverse section through the light conductors in the upper front surface of the rotor of the device, this section being taken along the plane 4—4 in FIG. 1.

DESCRIPTION OF A PREFERRED EMBODIMENT

The new testing device shown in FIG. 1 is for testing the rim around the apertures of upright standing bottles 2 for flaws such as chipping, cracks, roughness and so forth. The rim constitutes the sealing surface 3 which must be smooth and uniform if good seating and sealing is to be obtained when crown bottle caps are applied. The sealing surface 3 is formed by the upper annularly shaped rim of the aperture and is sometimes flat and sometimes rounded in cross-section, depending on the type of bottle.

The device 1 in FIG. 1 comprises a stationary base plate 4 which is arranged above the path of movement of the bottles 2. The bottles are translated by means of a transport-star 5 continuously in the direction of the arrow which is applied to the star. Base plate 4 has a bore on which a flanged internally cylindrical housing 7 is mounted. Ball bearings 8 are fitted into housing 7. The outer races of these bearings are stationary. The inner races are rotatable. A rotor 6 is mounted in bearings 8 for rotation. The axis of rotation 9 of rotor 6 is perpendicular to the plane 10 of the rim or sealing surface 3 of the bottle. During translational movement of bottles 2, the rotation axis 9 temporarily coincides with the axis of the bottle 2 which is also the axis of the sealing surface 3. Rotor 6 is rotated rapidly by means of a belt 11 driven by a motor 12. When the axes are coincident, the test cycle starts.

Two light-conductors 13 and 14 extend through rotor 6 generally axially. These light conductors are fiberoptic bundles in the actual device. Light-conductor 13 terminates in a lens 15 which projects light in the direction of the arrow toward the aperture plane 3. Light-conductor 14 receives light reflected from the rim or aperture of the bottle through a receiving lens 16. Thus, lens 15 is a light projector and lens 16 is a light receiver. As can be seen in FIG. 4, the light transmitting fiberoptic bundle 13 is annular in cross-section and the light receiver fiberoptic bundle 14 is simply circular. Thus, the two bundles 13 and 14 are arranged coaxially with each other where they pass through the cylindrical part of rotor 6 centrally of the inner races of bearings 8 which is the axis of rotation 9. The arrangement of the two light-conductors 13 and 14 and lenses 15 and 16 is such that the optical axis of the outlet lens 15 of the first light-conductor 13 (light transmitter) and the optical axis of the inlet end or lens 16 of the second light-conductor 14 (light receiver) lie in a common scanning plane 17. These optical axes are parallel to the axis of rotation 9 and they are spaced from this axis by the radial distance R in FIG. 3 of the sealing surface 3 from the center of the bottle. The plane of the optical axes is perpendicular to the aperture plane 10 and intersects the aperture plane tangentially to the center line of the sealing surface 3 as shown in FIGS. 1-3. Also, the optical axes of the light transmitter 13, 15 and of the light receiver 14, 16 is inclined by the acute angle alpha with respect to the aperture plane 10 and intersects the same. The angles alpha can lie in the range of ten to forty degrees but are most advantageously in the range between thirty and forty degrees. Smaller angles increase the ability of recognizing flaws but the adverse influence of the aperture being out of ideal position also increases, particularly its position in the vertical sense relative to rotor 6. With larger angles, the position error influence is less but at the expense of decreased sensitivity to flaw detection. It is not absolutely necessary for the scanning plane 17 to be exactly perpendicular to the aperture plane 10. The scanning plane can be tilted by a small amount relative to vertical without reducing the test accuracy.

The inspection field 18 that is illuminated momentarily by the transmitted light beam from the lens 15 is basically rectangular in shape and extends radially of the annular rim or sealing surface 3. The inspection field 18 can, however, also be angulated by the acute angle beta with respect to the central radius of the bottle whereupon the influence of radially extending seam lines or points on the test results is reduced. It is important that the radial dimension or width of inspection field 18 be greater than the corresponding width of the annular rim or sealing surface 3 as under test so that some shifting of the bottle from what might be called an ideal position can be tolerated.

The ends of the two light conductors 13 and 14 opposite from the lens 15 and 16 ends lie in the upper front surface of rotor 6 and extend at a right angle to the axis 9 of rotation. The light receiver conductor 14 is surrounded by the light transmitter conductor or fiberoptic bundle 13 where these conductors pass through the upper end of the rotor as previously alluded to. At the upper end of the device the light transmitting conductor 13 departs from concentricity with the light receiver conductor or fiberoptic bundle 14. Thus, the annular cross-section light transmitter bundle diverges over section 23 and connects to a source of light 24. The inside light receiver fiberoptic bundle 14 diverges at the top of the device and terminates in a section 21 that is optically coupled with a photosensitive or photoelectric element 22. The photosensitive element 22 puts out an electric signal whose amplitude is proportional to the intensity of the light that is reflected or scattered from the sealing surface 3 under test. The signals from the photosensitive device 22 are coupled to a comparator symbolized by the block marked 25. Comparator 25 is provided with a reference signal from a circuit symbolized by the block marked 26. The reference signal is variable or adjustable to set the threshold below which the comparator will produce a rejection signal. The comparator is coupled to a trigger circuit symbolized by the block marked 27. The comparator is also coupled to a rejection device, symbolized by the block marked 28. The rejection device causes ejection of defective or flawed bottles.

The trigger circuit 27 reacts to the position of the bottles 2 and regulates the test period which commences when the bottle center axis 9 is a little behind the axis of rotation of rotor 6. The testing route thus defined amounts to only a few millimeters. The rotation rate of rotor 6, the width of the inspection field 18 defined by means of a corresponding cross-section of the light-conductor 13 or a rectangular shutter opening, not shown, the translation speed of the bottles 2 and the testing route are determined with respect to one another in such manner that the rotor during the testing period carries out at least one complete revolution, and the sealing surface 3 thereupon does not permit the annular sealing surface to be missed by the orbiting or rotating inspection field 18.

The photosensitive element 22 during each scan produces a signal representative of the intensity of the radiation reflected by the sealing surface 3 which is intercepted by the light receiver 14, 16. The light intercepted and conducted by the light receiver 14, 16 has a predetermined intensity when the sealing surface 3 is flawless or in acceptable condition. If the sealing surface has one or more flaws then the radiation intensity intercepted by the light receiver 14, 16 drops significantly during the test cycle. Accordingly, the output signal of the photosensitive element 22 drops. If this drop exceeds a predetermined value as governed by the reference circuit or threshold regulator 26, then the evaluation device or comparator 25 produces a control signal that brings about actuation of ejection device 28 and the defective bottle 2 is rejected and isolated from the series of bottles that are passing through the test device.

In order to increase the output of the device by reducing the duration of each testing cycle, a second testing channel can be used as suggested by the dashed line diagrammatic showing of this channel in FIG. 2. Here another light transmitter 15a and light receiver 16a are arranged in a second scanning plane in the optical path of a second testing field 18a offset by 180° from the first testing field which scans the same channel. For this arrangement, a one-half revolution of rotor 6 is sufficient for making a complete scan of the rim around the bottle aperture. The second light-conductors can be branches of the first light-conductors which lead from two different inspection fields to a common photosensitive device. It is also possible to utilize additional light conductors and to conduct the reflected radiation to separate photosensitive devices which each produce signals for controlling defective bottle ejection devices.

Although a preferred embodiment of the invention has been described in detail, such description is intended to be illustrative rather than limiting, for the invention may be variously embodied and is to be limited only by interpretation of the claims which follow.

I claim:

1. A device for testing the sealing surface surrounding the apertures of bottles for flaws, comprising:
    a rotor and means for driving said rotor such that its axis of rotation is substantially perpendicular to the plane of said sealing surface during a test cycle,
    means mounted to said rotor and operative to project a beam of light onto said sealing surface and means mounted to said rotor for receiving light reflected from said sealing surface that is being tested for flaws, the optical axes of said light projecting and light receiving means lying in a common scanning plane which is substantially perpendicular to the sealing surface plane and which axes intersect the sealing surface plane within a first inspection field tangentially to the sealing surface plane and wherein the two optical axes are inclined at the same acute angle relative to said plane, and
    a photosensitive element optically coupled to said means for receiving the reflected light and being operative to produce electric signals that are proportional in amplitude to the intensity of the reflected light which intensity depends on whether or not there is a flaw in said sealing surface.

2. The device according to claim 1 wherein said acute angle at which said two optical axes are inclined is in the range of 30 to 40 degrees.

3. The device according to claim 1 wherein said acute angle at which the two optical axes inclined is in the range of 10 to 40 degrees.

4. The device according to any of claims 1, 2 or 3 wherein the inspection field (18) defined by the projected beam intersecting said sealing surface plane is rectangular in shape and has its length at an acute angle (B, beta) relative to a radius (R) of the aperture.

5. The device according to any of claims 1, 2 or 3 wherein said means for projecting a beam of light includes a lens and a light conductor to which the lens is coupled and which conductor extends through the rotor and a light source located externally of the rotor and optically coupled to said light conductor, and said means for receiving reflected light includes a lens and another light conductor to which the lens is coupled, said other light conductor extending through the rotor and optically coupled to said photosensitive element located externally of said rotor.

6. The device according to claim 5 wherein said one light conductor is circular in cross-section and the other light conductor is annular in cross-section at least where the conductors are optically coupled to said lenses, respectively.

7. The device according to any of claims 1, 2 or 3 including a second means mounted to the rotor for projecting light and a second means mounted to the rotor for receiving light arranged in such manner that the inspection field defined by the orbits over the same area of the sealing surface as the second inspection field is offset by 180 degrees with respect to the first inspection field.

8. The device according to claim 4 wherein said means for projecting a beam of light includes a lens and a light conductor to which the lens is coupled and which conductor extends through the rotor and a light source located externally of the rotor and optically coupled to said light conductor, and said means for receiving reflected light includes a lens and another light conductor to which the lens is coupled, said other light conductor extending through the rotor and optically coupled to said photosensitive element located externally of said rotor.

9. The device according to claim 4 including a second means mounted to the rotor for projecting light and a second means mounted to the rotor for receiving light arranged in such a manner that the inspection field defined by the orbits over the same area of the sealing surface of the second inspection field is offset by 180 degrees with respect to the first inspection field.

* * * * *